(12) United States Patent
Green et al.

(10) Patent No.: US 11,022,542 B2
(45) Date of Patent: Jun. 1, 2021

(54) ON-CHIP SPECTROSCOPIC SENSORS WITH OPTICAL FRINGE SUPPRESSION

(71) Applicants: INTERNATIONAL BUSINESS MACHINES CORPORATION, Armonk, NY (US); TRUSTEES OF PRINCETON UNIVERSITY, Princeton, NJ (US)

(72) Inventors: William Green, Yorktown Heights, NY (US); Chu Cheyenne Teng, Princeton, NJ (US); Gerard Wysocki, Princeton, NJ (US); Eric Zhang, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 7 days.

(21) Appl. No.: 16/504,100

(22) Filed: Jul. 5, 2019

(65) Prior Publication Data
US 2019/0331593 A1    Oct. 31, 2019

Related U.S. Application Data

(63) Continuation of application No. 15/914,455, filed on Mar. 7, 2018, now Pat. No. 10,578,547.
(Continued)

(51) Int. Cl.
*G01J 3/45* (2006.01)
*G01N 21/27* (2006.01)
(Continued)

(52) U.S. Cl.
CPC .............. *G01N 21/27* (2013.01); *G01J 3/28* (2013.01); *G01J 3/42* (2013.01); *G01J 3/45* (2013.01);
(Continued)

(58) Field of Classification Search
CPC ............... G01J 3/00; G01J 3/02; G01N 21/01
See application file for complete search history.

(56) References Cited

U.S. PATENT DOCUMENTS 7,359,802 B1 *  4/2008  Lewis ................ G01N 33/0031
                                                            702/24
7,361,501 B2    4/2008  Koo et al.
(Continued)

OTHER PUBLICATIONS

Chu C. Teng, et al., "Fiber-pigtailed silicon photonic sensors for methane leak detection," Conference on Lasers and Electro-Optics, OSA Technical Digest (online) (Optical Society of America, 2017), paper AM3B.2.
(Continued)

*Primary Examiner* — Jonathan M Hansen
(74) *Attorney, Agent, or Firm* — F. Chau & Associates, LLC

(57) ABSTRACT

An on-chip spectroscopic sensor includes a tunable diode laser. A laser driver for drives the tunable diode laser. An analyte test cavity receives a chemical sample and exposes the received chemical sample to light from the tunable diode laser. An optical detector detects light emerging from the analyte test cavity as a result of the laser exposure. A spectral analyzer determines a spectrum of the emerging light, matches and removes one or more known optical fringe patterns from the determined spectrum, and determines a composition or concentration of the chemical sample from the optical fringe pattern-removed spectrum.

12 Claims, 7 Drawing Sheets

Related U.S. Application Data

(60) Provisional application No. 62/506,376, filed on May 15, 2017.

(51) Int. Cl.
  *G01N 33/00* (2006.01)
  *G01N 21/39* (2006.01)
  *G01J 3/28* (2006.01)
  *G01J 3/42* (2006.01)

(52) U.S. Cl.
  CPC ......... *G01N 21/39* (2013.01); *G01N 33/0047* (2013.01); *G01J 2003/2869* (2013.01); *G01J 2003/423* (2013.01); *G01N 21/274* (2013.01); *G01N 2021/399* (2013.01); *G01N 2201/06113* (2013.01); *G01N 2201/1211* (2013.01)

(56) References Cited

U.S. PATENT DOCUMENTS

| | | |
|---|---|---|
| 9,163,984 B2 | 10/2015 | Nakamura |
| 10,241,033 B2 | 3/2019 | Uematsu et al. |
| 10,578,547 B2 * | 3/2020 | Green ................... G01N 21/39 |
| 2006/0197957 A1 * | 9/2006 | Jones ................... G01N 21/274 356/454 |
| 2010/0153014 A1 * | 6/2010 | Kischkat ............. G01V 11/002 702/6 |
| 2010/0211329 A1 * | 8/2010 | Farquharson .......... G01N 21/84 702/28 |
| 2012/0065948 A1 * | 3/2012 | Tan ...................... G01N 21/359 703/2 |
| 2016/0202119 A1 * | 7/2016 | Lee ........................ G01N 21/31 356/301 |
| 2018/0328840 A1 | 11/2018 | Green et al. |

OTHER PUBLICATIONS

Mar. 7, 2018, U.S. Appl. No. 15/914,455, U.S. Pat. No. 10,578,547.

* cited by examiner

ON-CHIP SPECTROSCOPIC SENSORS WITH OPTICAL FRINGE SUPPRESSION

CROSS-REFERENCE TO RELATED APPLICATIONS

The present application is a Continuation of co-pending U.S. patent application Ser. No. 15/914,455 filed on Mar. 7, 2018, which is based on provisional application Ser. No. 62/506,376, filed May 15, 2017, the entire contents of which are herein incorporated by reference.

GOVERNMENT LICENSE RIGHTS

This invention was made with government support under DE-AR0000540 awarded by the Department of Energy. The government has certain rights in the invention.

BACKGROUND

The present invention relates to spectroscopic sensors and, more specifically, to on-chip spectroscopic sensors with optical fringe suppression.

Natural gas is an important part of global energy generation. However, as natural gas is collected from wells and carried along pipes, there is a risk that methane may leak. Spectroscopic sensors may therefore be used to detect the presence of fugitive methane. While traditional spectroscopic sensors may be large, expensive and delicate, on-chip spectroscopic sensors have been developed.

On-chip spectroscopic sensors may utilize laser absorption spectroscopy (LAS) to determine an atomic and/or molecular composition of matter by analyzing the frequency properties of laser light passing through an analyte. However, as the laser light of various frequencies passes through the on-chip spectroscopic sensors, reflections of light from unwanted interfaces may lead to various standing wave interference patterns, which, if not properly accounted for, may lead to imprecise spectroscopy as the signal may appear to include oscillations. This effect may be known as optical fringing, or etaloning, as it is caused by the light circulating within an optical cavity, which is an etalon. The use of silicon photonic waveguides within the on-chip spectroscopic sensors may be particularly prone to optical fringes with difficult to predict patterns, owing to its relatively large thermo-optic coefficient.

SUMMARY

An on-chip spectroscopic sensor includes a tunable diode laser. A laser driver for drives the tunable diode laser. An analyte test cavity receives a chemical sample and exposes the received chemical sample to light from the tunable diode laser. An optical detector detects light emerging from the analyte test cavity as a result of the laser exposure. A spectral analyzer determines a spectrum of the emerging light, matches and removes one or more known optical fringe patterns from the determined spectrum, and determines a composition or concentration of the chemical sample from the optical fringe pattern-removed spectrum.

A method for performing spectroscopy includes using a spectroscopic sensor to acquire spectra over a temperature range. A plurality of optical fringe patterns are identified at regular temperature increments within the temperature range. The plurality of optical fringe patterns are stored within a database. The spectroscopic sensor is configured to remove background from subsequent acquisitions based on the database of optical fringe patterns.

A method for detecting fugitive methane gas includes installing a spectroscopic sensor apparatus into a calibration tool. The spectroscopic sensor apparatus within the calibration tool is used to identify a plurality of optical fringe patterns at regular temperature increments within a predetermined temperature range. The plurality of optical fringe patterns are stored within a database. The spectroscopic sensor apparatus is configured by constructing a background removal model that is configured to detect one or more of the plurality of optical fringe patterns while correcting for laser frequency ramping instabilities by allowing each of the plurality of optical fringe patterns to be stretched/contracted. The configured spectroscopic sensor apparatus is removed from the calibration tool. The configured spectroscopic sensor apparatus is installed to a final location. The spectroscopic sensor apparatus is installed at the final location to detect fugitive methane.

BRIEF DESCRIPTION OF THE SEVERAL VIEWS OF THE DRAWINGS

A more complete appreciation of the present invention and many of the attendant aspects thereof will be readily obtained as the same becomes better understood by reference to the following detailed description when considered in connection with the accompanying drawings, wherein.

DETAILED DESCRIPTION

Figure 1:
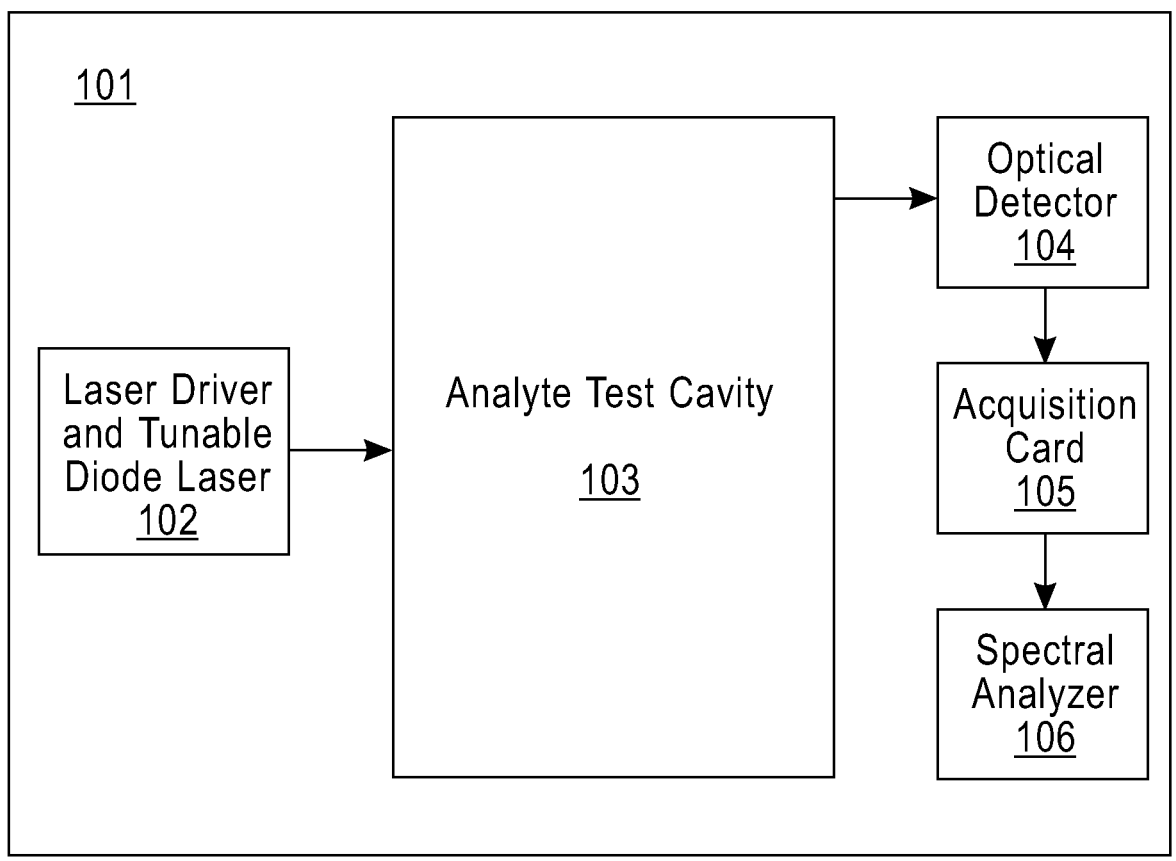
FIG. 1 is a schematic diagram illustrating a laser absorption spectroscopy (LAS) sensor in accordance with exemplary embodiments of the present invention.

In describing exemplary embodiments of the present invention illustrated in the drawings, specific terminology is employed for sake of clarity. However, the present invention is not intended to be limited to the illustrations or any specific terminology, and it is to be understood that each element includes all equivalents.

Exemplary embodiments of the present invention relate to an on-chip spectroscopic sensor having optical fringe suppression for removing the effects of fringes such as those caused by etalons. However, the apparatus and techniques discussed herein may be applied more generally to other spectroscopic sensors such as those that are non-integrated and operate in free-space.

As discussed above, various components of an on-chip spectroscopic sensor may be particularly affected by change in temperature. For example, silicon photonic waveguides having relatively large thermo-optic coefficient may be used. Accordingly, the nature of optical fringes may have a tendency to change as the temperature of the on-chip spectroscopic sensor changes. Exemplary embodiments of the present invention may therefor use a testing/calibrating apparatus to observe the effects of optical fringes for a particular on-chip spectroscopic sensor over a wide range of temperatures so that these effects may be identified, with respect to temperature. These tests may be performed without the presence of an analyte gas so as to observe baseline optical fringing. The on-chip spectroscopic sensor may thereafter be calibrated to identify and remove optical fringes that may be identified based on the testing/calibration data for that particular device. Additionally, by identifying the particular optical fringe pattern present, exemplary embodiments of the present invention may determine a temperature in use by determining which fringe pattern has been identified and/or removed.

It is to be understood, however, that even though exemplary embodiments of the present invention are discussed herein with respect to identifying and removing optical fringe patterns that are understood with respect to temperature, other operating conditions may be used to characterize optical fringe patterns, either instead of or in addition to temperature. Examples of other operating conditions may include pressure, humidity, etc.

FIG. 1 is a schematic diagram illustrating a laser absorption spectroscopy (LAS) sensor in accordance with exemplary embodiments of the present invention. While a simplified schematic is provided, it is to be understood that the LAS sensor may be embodied as an integrated on-chip silicon tunable diode laser absorption spectroscopy (IOS-TDLAS) apparatus, as a pigtailed waveguide sensor or as another suitable LAS sensor. The LAS sensor arrangement 101 may include a laser driver and a tunable diode laser driven therewith 102. The laser driver may be configured to drive the diode laser across a desired frequency spectrum. The laser light generated from the laser driver and a tunable diode laser driven therewith 102 may be directed to an analyte test cavity 103, which may be an exposed region in which ambient gas is permitted to enter.

In the analyte test cavity 103, the laser light may collide with gas molecules thereby exciting the gas molecules, which may then release photons of a particular wavelength as they relax. As the wavelength of the photons released may be characteristic for the gas within the analyte test cavity 103, an optical detector 104 may be used to sense the light emerging from the analyte test cavity 104 and an acquisition card 105 may be used to sample the optical detector 104 output, and transform the sampled signal into the frequency domain. A spectral analyzer 106 may then be used to identify the nature of the gas within the analyte test cavity 103 based upon the spectra observed, for example, to detect a presence of methane gas.

It is to be understood that various optical waveguides and other optical elements are included within the LAS sensor arrangement, for example, to guide light from the diode laser to the analyte test cavity, to guide light from the analyte test cavity to the optical detector, etc.

In practice, the above described detection approach may be complicated by the presence of background noise, such as the optical fringe patterns that are formed as light is reflected back and forth along the various optical waveguides and other optical elements. These fringe patterns may, at times, be difficult to isolate from the spectra resulting from the relaxation of the gas molecules, particularly as the optical characteristics of the particular LAS sensor arrangement provide unique fringe patterns. Moreover, the fringe patterns may have a tendency to change with ambient temperature, and various other ambient conditions.

Exemplary embodiments of the present invention therefore individually calibrate LAS sensor arrangements to ascertain the appearance of optical fringe patterns that are particular to the given LAS sensor arrangement under test. As these optical fringe patterns have a tendency to change with respect to temperature and various other ambient conditions, exemplary embodiments of the present invention construct a database or model the optical fringe patterns of the particular LAS sensor arrangement across a temperature range that the LAS sensor arrangement is likely to operate under.

Figure 2:
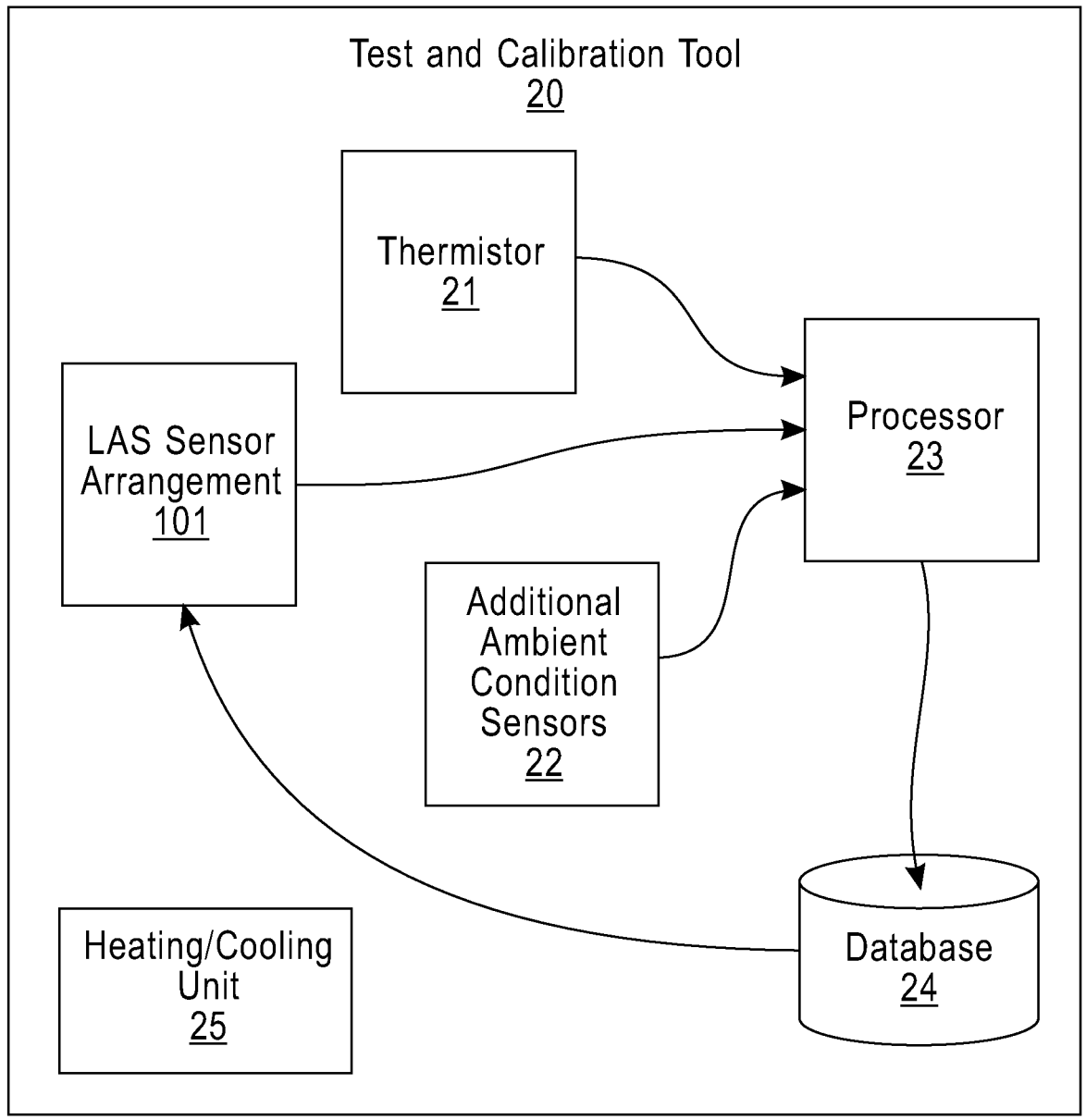
FIG. 2 is a schematic diagram illustrating a test and calibration tool for LAS sensor arrangements in accordance with exemplary embodiments of the present invention.

FIG. 2 is a schematic diagram illustrating a test and calibration tool for LAS sensor arrangements in accordance with exemplary embodiments of the present invention. The test and calibration tool 20 may include a region for receiving the LAS sensor arrangement 101 to be tested. The tool 20 may also include a thermistor 21 for monitoring ambient temperature, although the inclusion of the thermistor 21 may be omitted, as is described in greater detail below. One or more additional sensors 22 may also optionally be used for monitoring other ambient conditions such as pressure and humidity. During the testing and calibration process, the LAS sensor arrangement 101 is operational. An analyte gas may be substantially absent from the LAS sensor arrangement 101 or a known gas may be used. The resulting spectra acquired by the LAS sensor arrangement 101 may be provided to a processor 23 which may remove a known spectrum for the known gas, if one is used, and may store the results in a database 24 by temperature, as recorded by the thermistor 21, and by the other ambient conditions as measured by the additional sensors 22, if they are used. Alternatively, the results may be stored in the database 24 without being related to particular temperature and/or data from additional sensors 22.

Regardless of whether results are to be related to particular temperatures, testing may be performed for a period of time long enough to capture data across an entire temperature range that the LAS sensor arrangement 101 is likely to be operated within, however, a heating/cooling unit 25 may optionally be used to help span the desired temperature range.

The processor 23 may additionally use the data acquired from the LAS sensor arrangement 101, the thermistor 21, and the additional ambient condition sensors 22 (if used) to isolate the optical fringe patterns at each temperature and program (configure) the LAS sensor arrangement 101 to identify and remove the identified optical fringe patterns from data that is subsequently acquired during actual use (use that is not related to testing and configuration, for example, use in fugitive methane detection).

Figure 3:
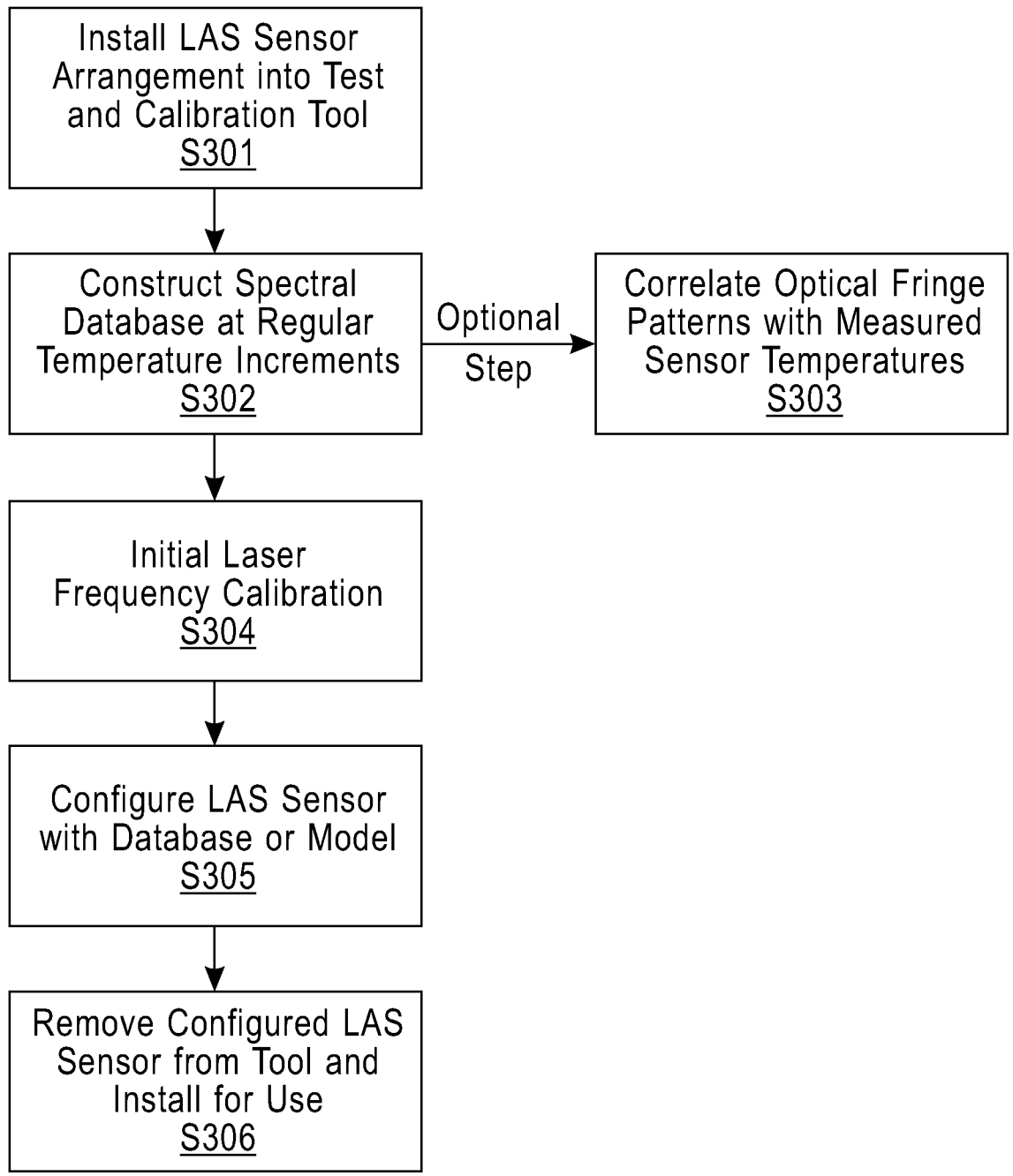
FIG. 3 is a flow chart illustrating an approach for performing fringe background removal calibration for an LAS in accordance with exemplary embodiments of the present invention.

FIG. 3 is a flow chart illustrating an approach for performing fringe background removal calibration for an LAS in accordance with exemplary embodiments of the present invention. The LAS sensor arrangement to be configured may be installed within a test and calibration tool (Step S301) such as the tool described above with respect to FIG. 2. Thereafter, the LAS sensor arrangement may be tested across a desired range of temperatures (Step S302). For example, testing may be performed from between 20° C. and 30° C. at intervals of $1\times10^{-4}$° C. However, it is to be understood that other temperature ranges may be used and other intervals may be used. The LAS sensor arrangement may be able to span the desired temperature range during the course of normal operation, however, a heating and/or cooling device may optionally be used to ensure that the full range of temperatures are achieved during testing and calibration.

The result of this calibration may be stored within a spectral database (Step S302). As mentioned above, while the spectra may be acquired over a particular temperature at regular temperature intervals, the results need not be correlated within the database according to temperature. However, as an optional step, the optical fringe patterns may be correlated, within the database, according to the particular temperature at which the particular optical fringe pattern was acquired (Step S303), and this may be accomplished, for example, by measuring temperature as spectra are observed, for example, using the thermistor 21.

It is noted that as the diode laser is tuned across the desired frequency range for performing LAS, laser ramping nonlinearities may impact the appearance of the optical fringe patterns and may make it more difficult to match the optical fringe patterns observed during calibration with those that might present during actual use. Accordingly, exemplary embodiments of the present invention may further allow correction of laser frequency ramping instabilities by allowing the measured fringe pattern to be stretched/contracted in order to better approximate the optical fringe patterns stored in the database. Once properly matched to the fringe database (linear or spline interpolation may be employed to stretch/contract the fringe pattern), a predetermined frequency axis (measured in Step S304) can be reliably used for concentration retrieval.

The LAS sensor arrangement may then be calibrated according to the database or mode (Step S305). This calibration step may include copying the database or model to local storage of the LAS sensor arrangement and configuring the LAS sensor arrangement to search for an identify the presence of one of the stored optical fringe patterns during use. The LAS sensor arrangement may be configured to remove optical fringe patterns, that have been identified, from sensor data so as to produce sensor data that is substantially free of optical fringe patterns. Once configuration has been completed, the LAS sensor arrangement may be removed from the tool and integrated into a final form, such as a tool for detecting fugitive methane (Step S306).

Figure 4:
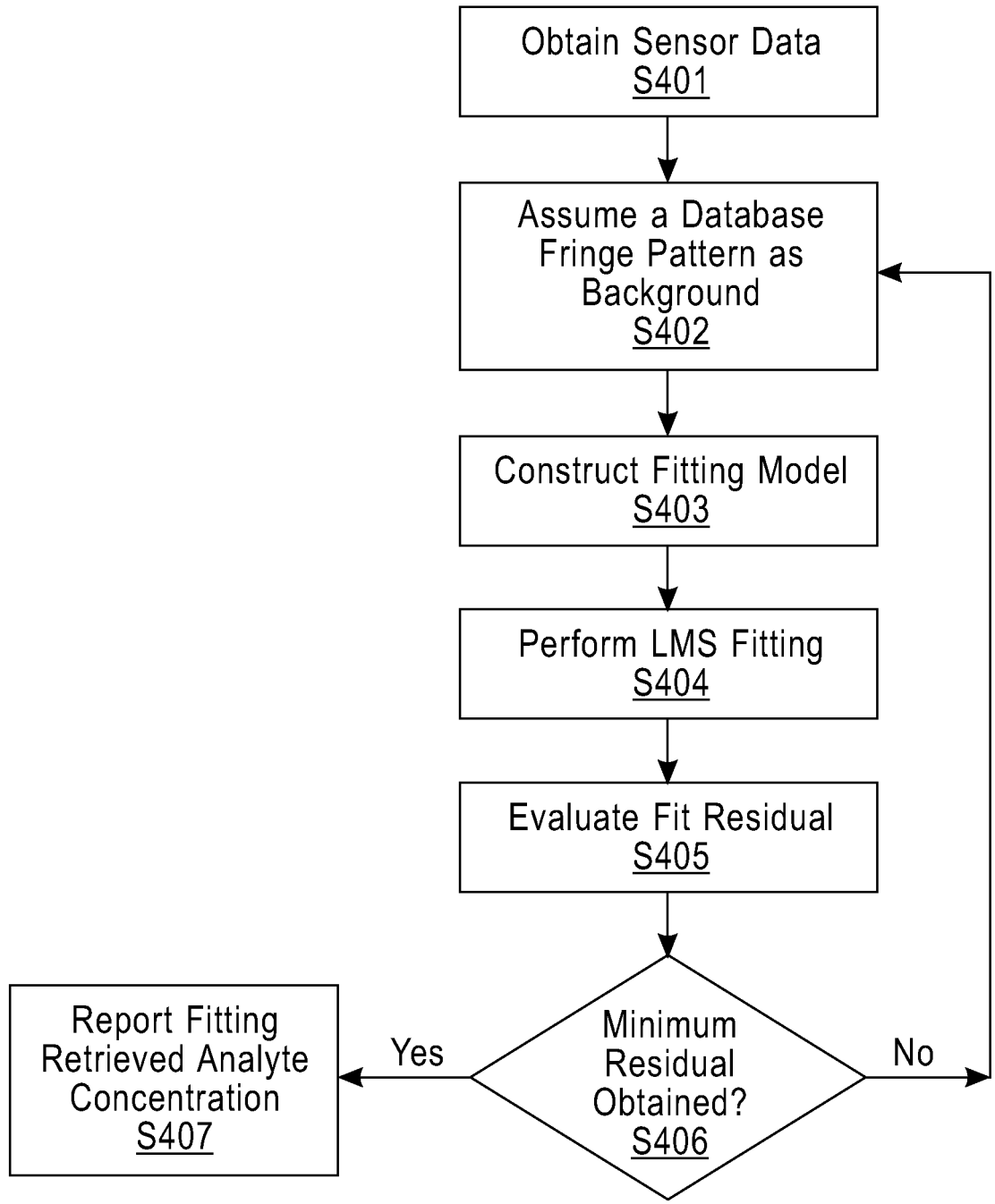
FIG. 4 is a flow chart illustrating an approach for performing fringe background removal with a calibrated LAS in accordance with exemplary embodiments of the present invention.

FIG. 4 is a flow chart illustrating an approach for performing fringe background removal with a calibrated LAS in accordance with exemplary embodiments of the present invention. The LAS sensor arrangement, having been calibrated, for example, according to the approach described above with reference to FIG. 3, may be used to obtain sensor data (Step S401). This may include, for example, tuning the diode laser across a desired frequency range, obtaining optical detector signal, and digitizing the optical detector signal. From there, the database of known optical fringe patterns may be drawn upon to identify an optical fringe pattern from the sensor data. The optical fringe patterns of the database, when closely matched to optical fringe patterns found in the obtained sensor data, represent background that is to be removed. Each optical fringe pattern in the database may be compared, for example, one-by-one, to the newly acquired spectrum (Step S402).

The correct database fringe pattern for the sensor data spectrum is determined by constructing a fitting model that allows least-mean-squares (LMS) fitting to be performed (Step S403).

The fitting model may be constructed, for example, using the following formula:

$$I_t(v(t))=I_0(v(t))\times e^{-\sigma(v(t))NL}\times \text{fringe background}$$

where $v(t)$ represents laser frequency as a function of time. In direct absorption spectroscopy, the laser frequency may be linearly tuned across the absorption line periodically. $I_t$ represents transmitted laser intensity or equivalently the measured spectrum. $I_0$ represents incident laser intensity, which for example can be modeled as a low-order polynomial to approximate changes in laser output intensity as laser frequency is being tuned. $\sigma$ represents cross section of light absorption by a single particle; and this value may be modeled using the absorption lineshape function and HITRAN absorption line parameters. L represents optical pathlength of the sensor. N represents analyte concentration. The fringe background represents a fringe pattern spectrum from the database. The fringe background may be configured to allow for the adjustment of laser frequency axis $v(t)$ during fitting to accommodate stretching and contraction of the fringe pattern, and can be implemented using linear interpolation of the measured spectrum.

Thereafter, least mean squared (LMS) fitting may be used to apply the constructed fitting model to the sensor data (Step S404). By performing LMS fitting, the following parameters of the fitting model may be determined: the adjusted laser frequency axis $v(t)$, the fringe background amplitude scaling, the incident laser intensity $I_0$, and the analyte concentration N.

As discussed above, the adjustment of the laser frequency axis $v(t)$ may be used to account for the effects that laser frequency shift may have on the appearance of the optical fringe patterns. In this way, the optical frequency axis may be calibrated to account for any laser frequency fluctuations or drift. The corrected frequency axis may then be used in the fitting of the absorption profile, which may ensure accurate concentration retrieval.

The results of the LMS fitting may then be evaluated to determine if there is a match between one of the known optical fringe patterns and the sensor data (Step S405). This may be performed, for example, by determining whether a minimum residual is obtained as a result of the LMS fitting (Step S406). If the minimum residual is not obtained (No, Step S406), then the next optical fringe pattern within the database may be checked against the sensor data, thereby repeating the process from Step S402 until a minimum residual is obtained (Yes, Step S406), thereby signifying a match between the optical fringe pattern being tested and the sensor data. Thereafter, the analyte concentration already retrieved during LMS fitting (Step S404) may be reported as the fringe-corrected concentration as the LMS fitting was performed with the best-match fringe background (Step S407).

Figure 5:
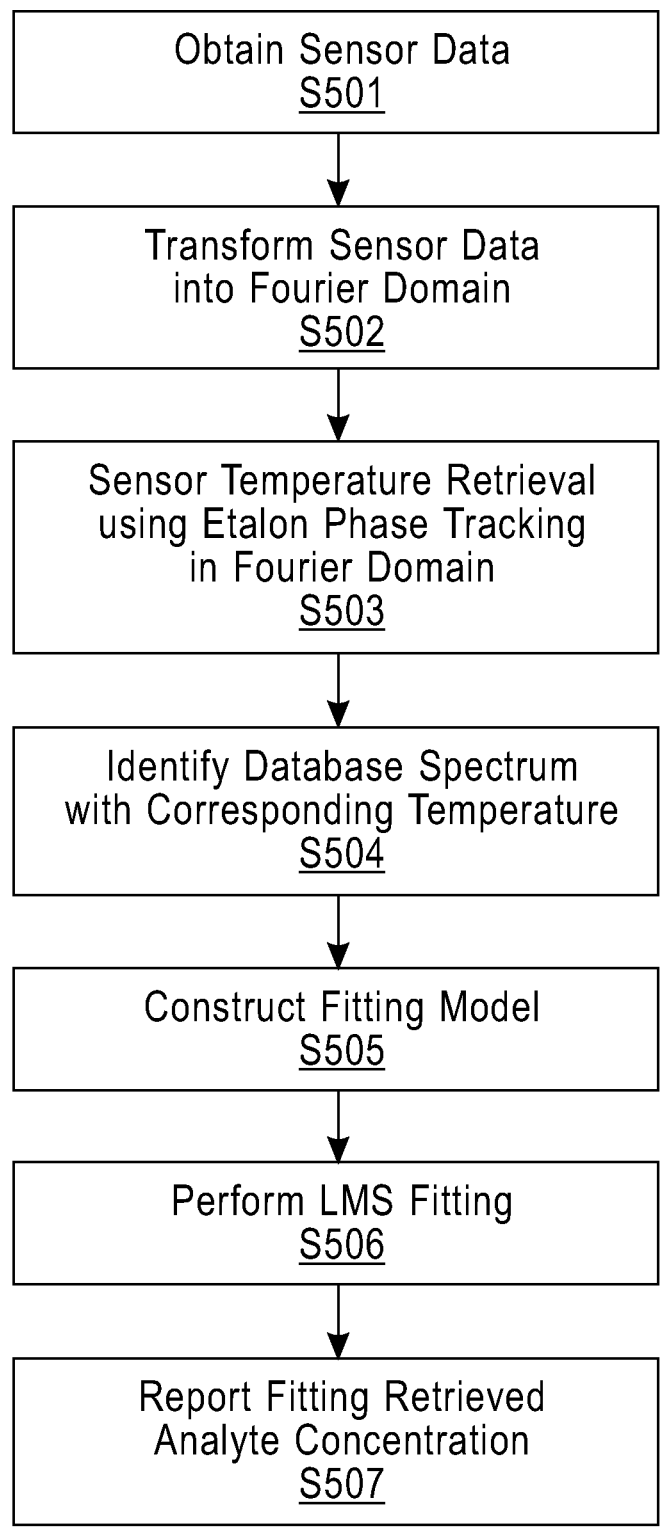
FIG. 5 is a flow chart illustrating another approach for performing fringe background removal with a calibrated LAS in accordance with exemplary embodiments of the present invention.

FIG. 5 is a flow chart illustrating another approach for performing fringe background removal with a calibrated LAS in accordance with exemplary embodiments of the present invention. According to this approach, calibration would have to include the optional step S303 discussed above in which optical fringe patterns were correlated with temperature. During sensing, the sensor data may be obtained (Step S501) and the obtained sensor data may be transformed into the Fourier domain (Step S502). The present temperature may be identified based on an observed optical fringe pattern within the obtained sensor data in the Fourier domain (Step S503). Specifically, the phase of the Fourier transformed spectrum corresponding to one or more etalon fringes may be used to quantify the amount of etalon drift (which is directly related to sensor temperature) in the sensor data compared to a prior time. Then, the optical fringe pattern associated with the determined temperature may be retrieved (Step S504) and used to construct a fitting model (Step S505) and then the fitting model may be used to perform LMS fitting on the obtained sensor data to produce the background-removed spectrum, which may be analyzed to determine analyte concentration (Step S506).

As mentioned in the approach above, the temperature of the LAS sensor may be determined by seeing which temperature is associated with the matched optical fringe pattern. The determined temperature may then be reported. According to some exemplary embodiments of the present invention, determining the temperature in this way may be used as a continuous on-chip temperature monitor. It is further noted that used as such, exemplary embodiments of the present invention may be used to determine temperature to a resolution equal to that used during calibration, which may be on the order of $1 \times 10^{-4}$° C., as described above, which may be significantly more accurate than other on-chip temperature measurement devices.

If the temperature is approximately known, for example, by the use of a thermistor incorporated into the LAS sensor arrangement, this approximate temperature may be used to narrow down the field of the matching so as to limit the search to known optical fringe patterns associated with temperatures within a particular range around the approximate temperature. For example, if the temperature is estimated to be 24° C., matching may be limited to +/±2° C. of the estimated temperature, which may be 22° C. to 26° C. By limiting the search range, the procedure described in FIG. 4 may be implemented faster and with reduced computational cost.

Figure 6:
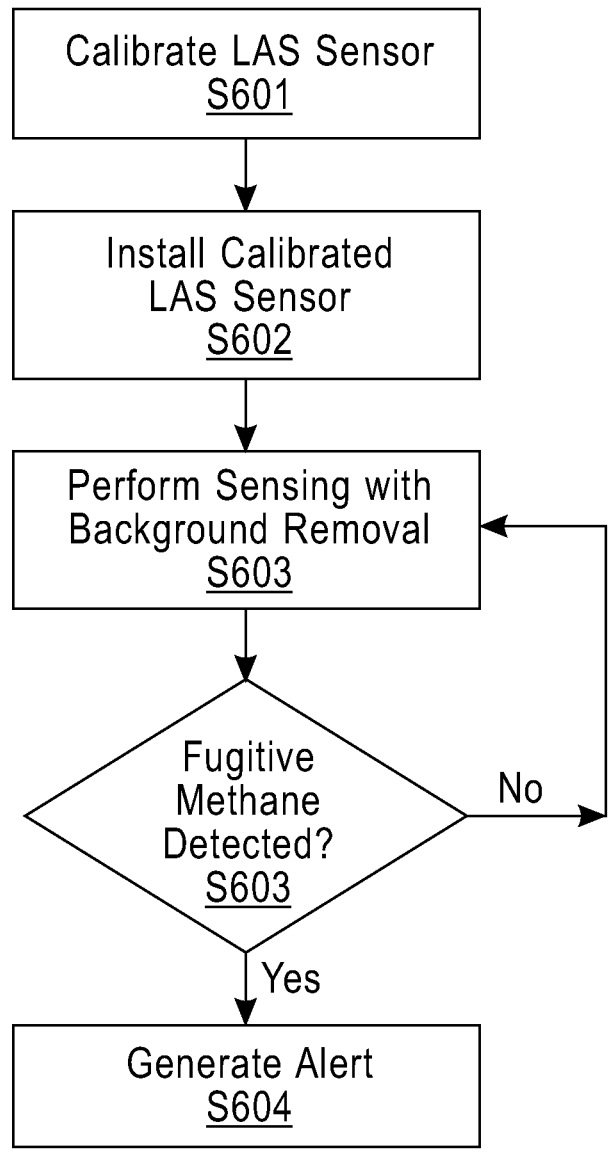
FIG. 6 is a flow chart illustrating a method for using a calibrated LAS sensor arrangement to detect fugitive methane gas in accordance with exemplary embodiments of the present invention.

According to either approach, the background-removed spectrum may be compared against known spectra, such as the known spectrum for methane, to determine if methane is present. FIG. 6 is a flow chart illustrating a method for using a calibrated LAS sensor arrangement to detect fugitive methane gas in accordance with exemplary embodiments of the present invention. First, the LAS sensor may be calibrated, for example, as discussed above (Step S601). Then, the calibrated LAS sensor may be installed along a path of methane supply lines or a facility handling methane (Step S602). The LAS sensors may be installed at locations where methane should not be, but would likely be found in the event of a leak. Sensing may then be continuously performed, using optical fringe pattern background removal, for example, as described in detail above (Step S603). The sensing may then be used to determine whether fugitive methane gas is detected (Step S603).

If it is determined that methane is present (Yes, Step S603), then an alert may be generated (Step S604). If methane is not determined to be present (No, Step S603) then the process may be repeated.

It is also noted that exemplary embodiments of the present invention may be used to identify and remove multiple different optical fringes from a single detection signal as different optical fringes may be present at different free spectral ranges (FSR) and it is understood that acquisition of sensor data (for both calibration and use) may be performed across a wide set of spectral ranges as the diode laser is tuned. Additionally, the presence of multiple optical fringes may be used to determine that different parts of the LAS sensor arrangement may have different temperatures, and to identify the different temperature at each part of the LAS sensor arrangement.

The alert, so generated, may take the form of an audible and/or visual alert such as an alarm. Speakers and lights may be used to implement such an alarm. Alternatively, or additionally, the alert may be embodied as an automatically generated email and/or text message that is transmitted to a mobile device of an operator, for example, over a wireless network.

Figure 7:
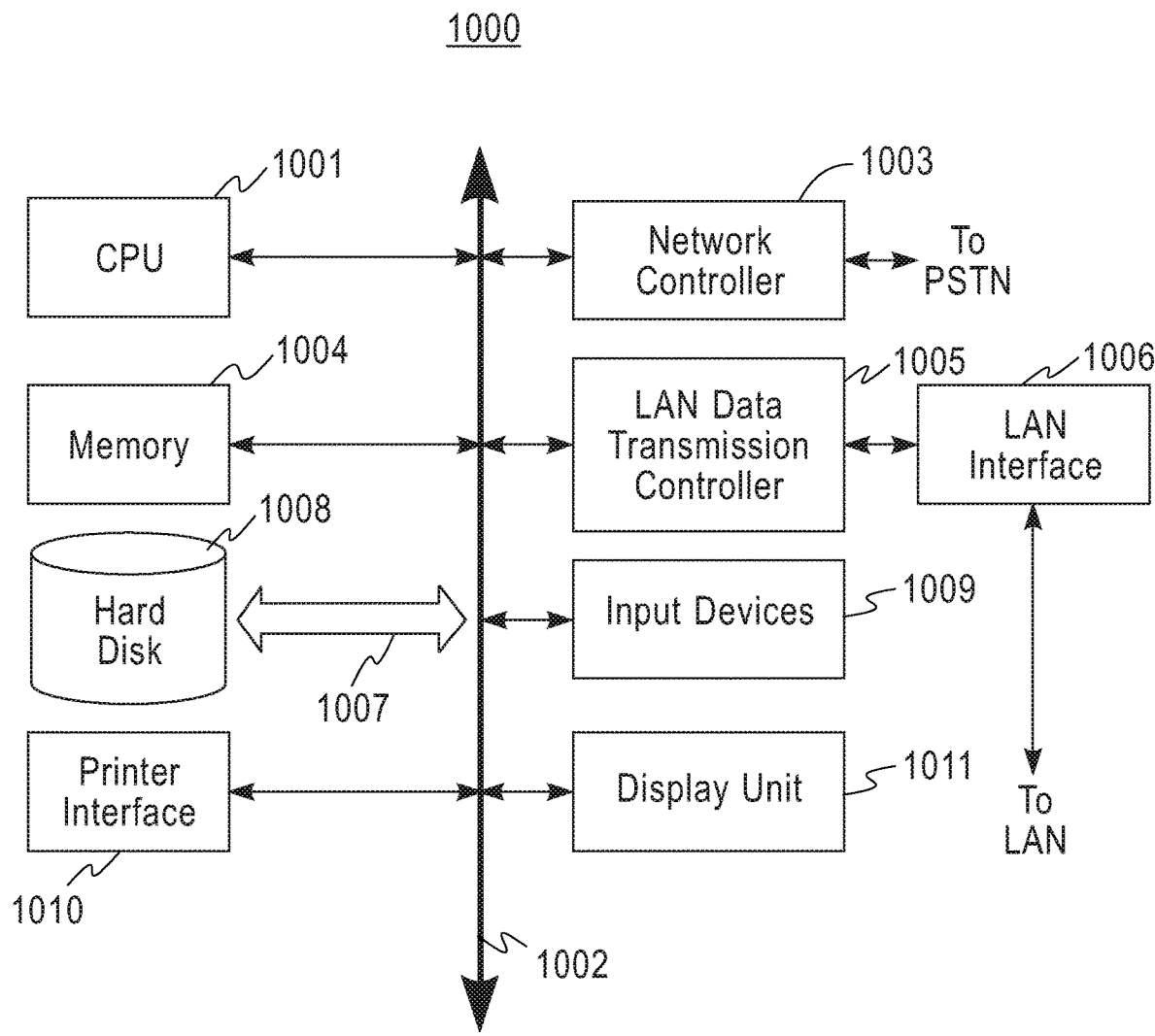
FIG. 7 shows an example of a computer system capable of implementing the method and apparatus according to embodiments of the present disclosure.

FIG. 7 shows another example of a system in accordance with some embodiments of the present invention. By way of overview, some embodiments of the present invention may be implemented in the form of a software application running on one or more (e.g., a "cloud" of) computer system(s), for example, mainframe(s), personal computer(s) (PC), handheld computer(s), client(s), server(s), peer-devices, etc. The software application may be implemented as computer readable/executable instructions stored on a computer readable storage media (discussed in more detail below) that is locally accessible by the computer system and/or remotely accessible via a hard wired or wireless connection to a network, for example, a local area network, or the Internet.

Referring now to FIG. 7, a computer system (referred to generally as system 1000) may include, for example, a processor e.g., central processing unit (CPU) 1001, memory 1004 such as a random access memory (RAM), a printer interface 1010, a display unit 1011, a local area network (LAN) data transmission controller 1005, which is operably coupled to a LAN interface 1006 which can be further coupled to a LAN, a network controller 1003 that may provide for communication with a Public Switched Telephone Network (PSTN), one or more input devices 1009, for example, a keyboard, mouse etc., and a bus 1002 for operably connecting various subsystems/components. As shown, the system 1000 may also be connected via a link 1007 to a non-volatile data store, for example, hard disk, 1008.

In some embodiments, a software application is stored in memory 1004 that when executed by CPU 1001, causes the system to perform a computer-implemented method in accordance with some embodiments of the present invention, e.g., one or more features of the methods, described with reference to FIGS. 3 and 4.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Exemplary embodiments described herein are illustrative, and many variations can be introduced without departing from the spirit of the invention or from the scope of the appended claims. For example, elements and/or features of different exemplary embodiments may be combined with each other and/or substituted for each other within the scope of this invention and appended claims.

What is claimed is:

1. A method for performing spectroscopy, comprising:
   using a spectroscopic sensor to acquire spectra at a plurality of different temperatures at regular temperature increments over a temperature range;
   identify temperature-dependent etalon patterns at each of the regular temperature increments within the temperature range;
   store the identified temperature-dependent etalon patterns at each of the regular temperature increments within a database;
   measure an ambient temperature at a time of subsequent acquisition;
   use the spectroscopic sensor to acquire a subsequent spectra;
   retrieve, from the database, the temperature-dependent etalon patterns for the ambient temperature at the time of subsequent acquisition;

remove the temperature-dependent etalon patterns for the ambient temperature at the time of subsequent acquisition from the acquired subsequent spectra.

2. The method of claim 1, further comprising:
determining a composition or concentration of gas sample from the temperature-dependent etalon pattern-removed subsequent spectrum.

3. The method of claim 2, further comprising using the determined composition or concentration of the gas sample to detect fugitive methane.

4. The method of claim 2, wherein retrieving, from the database, the temperature-dependent etalon patterns for the ambient temperature at the time of subsequent acquisition comprises:
constructing a fitting model for the temperature-dependent etalon patterns for the ambient temperature at the time of subsequent acquisition;
applying the one constructed fitting model to the acquired subsequent spectra by performing least mean square (LMS); and
evaluating a fit residual of the applied fitting model.

5. A method for detecting fugitive methane gas, comprising:
installing a spectroscopic sensor apparatus into a calibration tool;
using the spectroscopic sensor apparatus within the calibration tool to identify a plurality of different temperature-dependent etalon patterns at regular temperature increments within a predetermined temperature range;
store the plurality of temperature-dependent etalon patterns within a database;
configure the spectroscopic sensor apparatus by constructing an etalon removal model that is configured to measure an ambient temperature at a time of subsequent acquisition, use the spectroscopic sensor apparatus to acquire a subsequent spectra, retrieve, from the database, the temperature-dependent etalon patterns for the ambient temperature at the time of subsequent acquisition, adjust the retrieved temperature-dependent etalon patterns by correcting for laser frequency ramping instabilities by allowing each of the retrieved temperature-dependent etalon patterns to be stretched/contracted;
removing the configured spectroscopic sensor apparatus from the calibration tool;
installing the configured spectroscopic sensor apparatus to a final location; and
using the spectroscopic sensor apparatus installed at the final location to detect fugitive methane.

6. The method of claim 5, wherein using the spectroscopic sensor apparatus to detect fugitive methane includes:
acquiring the subsequent spectra causing the spectroscopic sensor apparatus;
removing background from the acquired subsequent spectrum using the constructed etalon removal model; and
identifying the presence of fugitive methane by analyzing the background-removed spectrum.

7. The method of claim 5, wherein the predetermined temperature range is from 20° C. to 30° C. and the regular temperature intervals are $1 \times 10^{-4}$° C.

8. The method of claim 5, wherein configure the spectroscopic sensor apparatus further includes copying the database to the spectroscopic sensor apparatus.

9. The method of claim 5, wherein the etalon removal model allows for least-mean-squares (LMS) fitting.

10. The method of claim 6, wherein the etalon removal model is constructed using the formula:

$$I_t(v(t)) = I_0(v(t)) \times e^{-\sigma(v(t))NL} \times \text{fringe background}$$

where $v(t)$ represents laser frequency as a function of time, $I_t$ represents transmitted laser intensity or equivalently the measured spectrum, $I_0$ represents incident laser intensity, $\sigma$ represents cross section of light absorption by a single particle, L represents optical pathlength of the sensor, and N represents analyte concentration.

11. The method of claim 5, wherein the final location is a methane conduit or facility handling methane.

12. A method for determining ambient temperature in spectroscopy, comprising:
using a spectroscopic sensor to acquire spectra;
identifying a temperature-dependent etalon pattern from the acquired spectra;
searching a database of temperature-dependent etalon patterns indexed by temperature to find a match for the identified temperature-dependent etalon pattern; and
determining an ambient temperature based on a temperature index of the matched temperature-dependent etalon pattern.

* * * * *